United States Patent
Meier et al.

(10) Patent No.: US 6,998,140 B2
(45) Date of Patent: Feb. 14, 2006

(54) DISPERSION COMPRISING A NON-IONIC EMULSIFIER

(75) Inventors: Christian Meier, Darmstadt (DE);
Johanna Eisele, Darmstadt (DE);
Michael Schnabel, Biebesheim (DE);
Klaus Schultes, Wiesbaden (DE);
Stefan Grimm, Worms (DE);
Hans-Ulrich Petereit, Darmstadt (DE);
Thomas Suefke, Erzhausen (DE)

(73) Assignee: Roehm GmbH & Co. KG, Darmstadt (DE)

(*) Notice: Subject to any disclaimer, the term of this patent is extended or adjusted under 35 U.S.C. 154(b) by 642 days.

(21) Appl. No.: 09/926,484

(22) PCT Filed: Feb. 2, 2001

(86) PCT No.: PCT/EP01/01108

§ 371 (c)(1),
(2), (4) Date: Nov. 9, 2001

(87) PCT Pub. No.: WO01/68767

PCT Pub. Date: Sep. 20, 2001

(65) Prior Publication Data

US 2003/0060381 A1 Mar. 27, 2003

(30) Foreign Application Priority Data

Mar. 10, 2000 (DE) .............................. 100 11 447

(51) Int. Cl.
A61K 9/16 (2006.01)
A61K 9/14 (2006.01)

(52) U.S. Cl. ..................................... 424/490; 424/489

(58) Field of Classification Search ................ 424/490, 424/489
See application file for complete search history.

(56) References Cited

U.S. PATENT DOCUMENTS

| 4,259,315 A * | 3/1981 | Lippmann et al. |
| 6,632,454 B1 | 10/2003 | Beckert et al. |
| 2003/0152627 A1 | 8/2003 | Beckert et al. |
| 2005/0079216 A1 | 4/2005 | Petereit et al. |
| 2005/0089571 A1 | 4/2005 | Beckert et al. |

FOREIGN PATENT DOCUMENTS

| DE | 199 18 435 | 1/2000 |
| EP | 0 315 218 | 5/1989 |
| JP | 01-113322 | * 5/1989 |
| JP | 1-113322 | 5/1989 |

OTHER PUBLICATIONS

Achim Göpferich, et al., Journal of Controlled Release, vol. 18, No. 2, pp. 133-144, "The Influence of Endogenous Surfactant on the Structure and Drug-Release Properties of Eudragit NE30D-Matrices", Feb. 1992.

* cited by examiner

Primary Examiner—Thurman K. Page
Assistant Examiner—Humera N. Sheikh
(74) Attorney, Agent, or Firm—Oblon, Spivak, McClelland, Maier & Neustadt, P.C.

(57) ABSTRACT

The invention relates to a dispersion suitable for use as coating agent and binder for pharmaceutical forms, having a solids content of 10–70% by weight consisting of
a) from 90 to 99% by weight of a methacrylate copolymer consisting of at least 90% by weight of (meth)acrylate monomers containing neutral radicals and having a glass transition temperature Tg of from −20° C. to +20° C. as determined by the DSC method, and
b) 1–10% by weight of a nonionic emulsifier having an HLB of from 15.2 to 17.3.

19 Claims, 2 Drawing Sheets

Release curve of KCl crystals coated with inventive dispersion

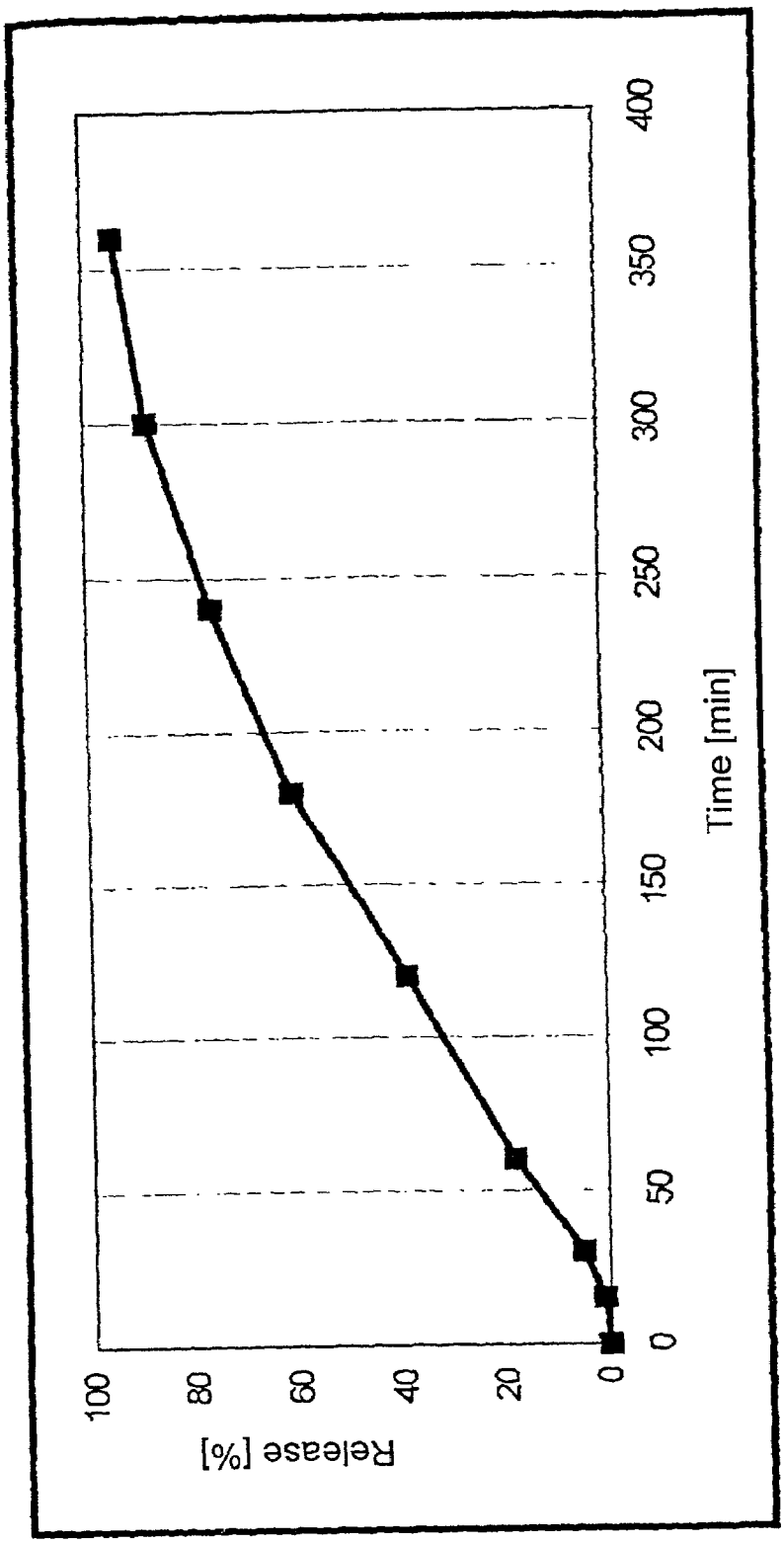
Figure 1: Release curve of KCl crystals coated with inventive dispersion

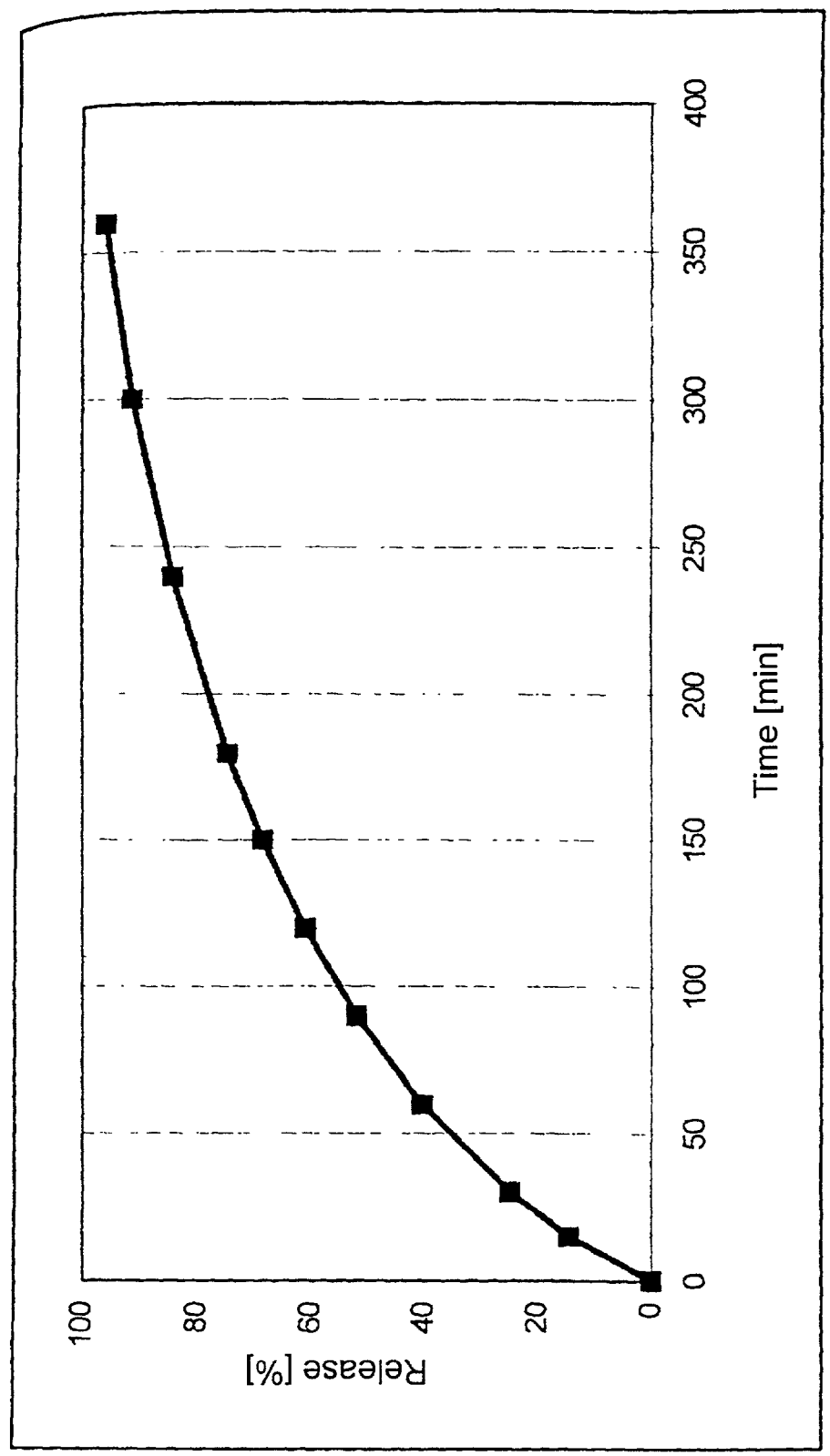
Figure 2 : Release curve of diprophylline matrix tablets

DISPERSION COMPRISING A NON-IONIC EMULSIFIER

This application claims priority to German Application No. 100 11 447.4, filed Mar. 10, 2001. This application is a 371 of PCT/EP01/01108, filed Feb. 2, 2001.

The invention relates to the field of dispersions and to their use as coating agents and binders for pharmaceutical forms.

PRIOR ART

The use of so-called neutral methacrylate copolymers, i.e. methacrylate copolymers consisting predominantly of (meth)acrylate monomers with neutral radicals, such as methyl methacrylate or ethyl methacrylate as coating agents and binders for pharmaceutical forms with delayed active-substance release has been known for a long time.

Uses in mixtures with anionic dispersions are described, for example, in EP-A 152 038, EP-A 208 213 or EP-A 617 972.

The neutral methacrylate copolymers are nowadays used preferably as dispersions. Dispersions of this kind are prepared by emulsion polymerization and therefore include as a result of their preparation an emulsifier, which also brings about the stability of the resulting dispersion per se. In the finished pharmaceutical form, moreover, the emulsifier present influences the active substance release characteristics.

As a result of the intended use in pharmaceuticals, and on account of the fact that owing to the monomer composition the copolymers have few if any charges, the selection of appropriate emulsifiers is very limited.

Göferich and Lee in "*The influence of endogenous surfactant on the structure and drug-release properties of Eudragit NE30D matrices*", Journal of Controlled Release 18 (1992), pp. 133–144, describe how an emulsifier of the nonylphenol type present in the dispersion causes problems for the release of active substance from coated pharmaceutical forms. The authors describe an anisotropic structure in copolymer films obtained from the dispersion. Both in films containing active substance and in films free of active substance, phase separation and crystallization of the emulsifier occur as a function of the storage period and the active substance content. These occurrences obviously result in inconsistencies in the release of the active substance clenbuterol. If the emulsifier is removed from freeze-dried copolymer by washing with water, then a uniform—although slowed—release of active substance is observed in the purified copolymer.

DE-A 195 03 099 describes a process for preparing aqueous addition-polymer dispersions by the method of free-radical aqueous emulsion polymerization in the presence of a nonionic emulsifier. Suitable nonionic emulsifiers are those whose cloud point is situated below the polymerization temperature. A large number of suitable compounds is listed, including nonylphenol emulsifiers.

Problem and Solution

The problem was seen to be to improve prior art dispersions comprising methacrylate copolymers with small or no fractions of monomers containing ionic radicals in such a way that, while retaining the stability of the dispersion and its particle size distribution, it is possible to use it to prepare medicament formulations in which phase separation with the formation of crystal structures as a result of the emulsifier does not occur. At the same time, there should be no deleterious alteration to the active substance release characteristics and other properties—mechanical properties, for example.

This problem has been solved by means of a dispersion suitable for use as a coating agent and binder for pharmaceutical forms, having a solids content of 10–70% by weight consisting of a) from 90 to 99% by weight of a methacrylate copolymer consisting of at least 90% by weight of (meth)acrylate monomers containing neutral radicals and having a glass transition temperature Tg of from –25° C. to +20° C. as determined by the DSC method (ISO 11357), and b) 1–10% by weight of a nonionic emulsifier having an HLB of from 15.7 to 16.2.

BRIEF DESCRIPTION OF THE DRAWINGS

FIG. 1 illustrates a release curve of KCl crystals coated with inventive dispersion.

FIG. 2 illustrates a release curve of diprophylline matrix tablets.

Implementation of the Invention

Methacrylate Copolymer

The dispersion of the invention comprises 90–99% by weight, based on the solids content, of a methacrylate copolymer.

The methacrylate copolymer consists of at least 90, in particular 95, preferably 97, in particular 99, with particular preference 100% by weight of (meth)acrylate monomers containing neutral radicals, especially $C_1$ to $C_4$ alkyl radicals.

Examples of suitable monomers are methyl methacrylate, ethyl methacrylate, butyl methacrylate, methyl acrylate, ethyl acrylate and butyl acrylate. Preference is given to methyl methacrylate, ethyl acrylate and methyl acrylate.

In small fractions, not more than 10, preferably not more than 5, with particular preference not more than 3 or not more than 1% by weight, methacrylate monomers containing anionic radicals, e.g. methacrylic acid, may be present.

The methacrylate copolymer has a glass transition temperature Tg of from –25° C. to +20° C., preferably from –10° C. to 0° C., determined by the DSC method (ISO 11357).

A typical methacrylate copolymer may be composed, for example, of 25–35% by weight methyl methacrylate and from 75 to 65% by weight ethyl acrylate.

In accordance with the invention, the polymers—which are neutral per se—may include small amounts of methacrylic acid, which although causing virtually no alteration in the water-insolubility of the polymer may nevertheless influence swelling and permit pH-dependent control of the permeability.

Emulsifiers

The dispersion of the invention contains from 1 to 10, preferably from 2 to 8, with particular preference from 4 to 6% by weight, based on the solids content, of a nonionic emulsifier having an HLB of from 15.7 to 16.2.

Emulsifiers control the course of the emulsion polymerization process by permitting the chain-building reaction of the emulsified monomers in the water phase. They therefore constitute an auxiliary which is necessary for the preparation and which determines the properties of the dispersion. They cannot normally be replaced without fundamental changes in relevant properties of the dispersion.

The HLB, introduced by Griffin in 1950, is a measure of the hydrophilicity of lipophilicity of nonionic surfactants. It may be determined experimentally by the phenol titration method of Marszall; cf. "Parfümerie, Kosmetik", Volume 60, 1979, pp. 444–448; further literature references are in Römpp, Chemie-Lexikon, 8th ed. 1983, p. 1750. See also, for example, U.S. Pat. No. 4,795,643 (Seth).

An HLB (hydrophilic/lipophilic balance) can be determined exactly only for nonionic emulsifiers. For anionic emulsifiers, this value may be determined arithmetically but is virtually always above or well above 20.

The HLB values in emulsifiers have a distinct influence on the crystallization of the emulsifier. Ideally these values are between 15.7 and 16.2. Above the claimed range, the emulsifiers crystallize out after drying. Emulsifiers having an HLB below the claimed range are unable to stabilize the dispersion sufficiently, which is evident from severe coagulation. The HLB values were either taken from the literature (Fiedler: Lexikon der Hilfsstoffe) or calculated in accordance with W. C. Griffin (supplement from Parfümerie and Kosmetik 64, 311–314, 316 (1983); Hüthig Verlag, Heidelberg/Pharm. Ind. 60 No. 1 (1998); dielectricity thermoanalysis).

The emulsifier is to be toxicologically unobjectionable, and therefore nonionic emulsifiers are preferred.

Suitable emulsifier classes are ethoxylated fatty acid esters or ethers, ethoxylated sorbitan ethers, ethoxylated alkylphenols, glycerol esters or sugar esters, or wax derivatives.

Suitable emulsifiers are, for example, polyoxyethyleneglycerol monolaurate, polyoxyethyleneglycerol monostearate, polyoxyethylene-20-cetyl stearate, polyoxyethylene-25-cetyl stearate, polyoxyethylene(25)-oxypropylene monostearate, polyoxyethylene-20-sorbitan monopalmitate, polyoxyethylene-16-tert-octylphenol, polyoxyethylene-20-cetyl ether, polyethylene glycol(1000) monocetyl ether, ethoxylated castor oil, polyoxyethylene sorbitol-lanolin derivatives, polyoxyethylene(25)propylene glycol stearate and polyoxyethylenesorbitol esters.

Preference is given to polyoxyethylene-25-cetyl stearate, polyoxyethylene-20-sorbitan monopalmitate, polyoxyethylene-16-tert-octylphenol and polyoxyethylene-20-cetyl ether.

Preparation of the Dispersion

The novel dispersion is obtained in a manner known per se by aqueous emulsion polymerization by the batch technique or the feed technique, semi-continuously or else continuously (in this respect see, for example, DE 195 03 099 A1).

The free-radical polymerization of the monomers in the presence of the emulsifier takes place by means of radical-forming water-soluble polymerization initiators, it being possible for radical formation to take place thermally or by way of redox processes. If desired, molecular weight regulators are added for the purpose of adjusting the molar masses. Emulsion polymers are commonly prepared in concentrations between 10 and 70% by weight. A solids content of 30–50% by weight is advantageous. Batchwise preparation generally takes place in stirred tank reactors.

For the preparation, in the case of a simple batch preparation, all monomers are charged to a reaction vessel in accordance with the desired copolymer composition, together with the emulsifier, initiators, regulators and other auxiliaries and together with water, and are dissolved or dispersed therein. By activating the initiator (increasing the temperature, adding the redox agent), the polymeric chain reaction is initiated and conducted. In the course of this reaction, the known latex particles, consisting of polymer chains, are formed.

Antifoam emulsion and stabilizers may be added to the dispersion.

Uses

The novel coating agents may be processed correspondingly like other known aqueous, acrylate-based coating agents. The most common coatings are coatings on particles with a size of from 0.1 to 3 mm by the fluid-bed coating process. Customary additions, such as pigments, fillers, thickeners, defoamers, preservatives, etc., may be used in customary amounts. Coatings may be produced on plain tablets, capsules, film-coated tablets, granules or crystals. The formation of matrix tablets or matrix granules is also possible. Preferred processing temperatures are situated within the range from 20 to 40° C. Suitable film thicknesses are from 10 to 80 micrometers.

By means of the coating film, the mechanism of active substance release by diffusion may be utilized not only in the gastrointestinal tract but also in other body cavities, tissues, blood circulations and the habitats of animals and plants for the purpose there of inducing delayed release of active substances. Examples are films which are introduced into the blood circulation using catheters, and implants of veterinary pharmaceuticals.

As with other aqueous coating agents, coats of multi-layer coating systems may be produced. For example, a core containing, for example, basic or water-sensitive active substances may be provided with an insulating coat of another coating material, such as cellulose ether, cellulose ester, cationic polymethacrylates (such as EUDRAGIT® E100, -RL 100, RS 100, Röhm GmbH) before the coating agent of the invention is applied. Likewise, further coatings, with for example an odour-masking or paste-concealing effect or with an appealing colour or gloss effect, may be applied subsequently.

The release characteristics of pharmaceutical coatings in vitro are tested in accordance with USP normally with artificial gastric fluid (0.1N HCl) and artificial intestinal fluid (pH 6.8).

Further applications are described in the following literature:

Bauer, Lehmann, Osterwald, Rothgang: Coated Dosage Forms, CRC Press LLC, Boca Raton, Fla., Medpharm Scientific Publishers, Suttgart 1998

I. Ghebre-Sellassie, Multiparticulate Oral Drug Delivery, Marcel Dekker, Inc. New York, Basle, Hong Kong, 1994

Spray Applications of Mixtures with Other Dispersions:

K. Lehmann, D. Dreher: Mixtures of Aqueous Polymethacrylate Dispersions for Drug Coating, Drugs made in Germany 31 101–102 (1988)

Matrix Tablets by Wet Granulation

K. Lehmann, H. -U. Petereit, Verwendung wäβriger Poly (meth)acrylat-Dispersionen für die Herstellung von Matrixtabletten [Use of aqueous poly(meth)acrylate dispersions for producing matrix tablets], Acta Pharm. Technol. 34(4) 189–195 (1988)

J. McGinity, Aqueous Polymeric Coatings for Pharmaceutical Dosage Forms, 2nd Edition, Marcel Dekker, Inc. New York, Basle, Hong Kong, 1996

Disintegrating Delayed-Release Tablets

K. Lehmann, H. -U. Petereit, D. Dreher, Schnellzer-fallende Tabletten mit gesteuerter Wirkstoffabgabe [Fast-disintegrating tablets with controlled active substance release], Pharm. Ind. 55, (10) 940–947 (1993)

K. Lehmann, H. -U. Petereit, D. Dreher, Fast Disintegrating Controlled Release Tablets from Coated Particles, Drugs Made in Germany 37(2), 53–60 (1994)

R. Bodmeier, Tabletting of Coated Pellets Eur. J. Phar and Biopharm. 431–8 (1997)

(Trans)Dermal Therapy Systems

Heilmann, K.: Therapeutische Systeme, Ferdinand Euler Verlag, Stuttgart, pp. 52–57.

Brandau, R. and Lippold, B. H. (1982): Dermal and Transdermal Absorption. Wissenschaftliche Verlags-gesellschaft mbH, Stuttgart, pp. 171–200.

H. -U. Petereit, 3rd European Congress of Biopharmaceutics and Pharmacokinetics-Proceed. Vol. I, 84–93 (1987)

Use of the Solid:

The solid obtained from the dispersions of the invention by drying, coagulation or pinch-off extrusion may be used as follows:

Extrusion: after blending with auxiliaries and/or active substances, if desired, to give granules, films and the like.

Injection moulding: in accordance with the new injection moulding application, to give hollow articles and monolithic carriers.

Dissolution: the polymer is soluble in customary solvents such as short-chain alcohols or ketones. Such solutions may be employed in customary coating processes.

Advantageous Effects of the Invention

The dispersions of the invention are used as coating agents and binders in the production of medicaments. Primarily, therefore, it is necessary to achieve the physicochemical properties necessary for this effect (see example 4 and 5). Particularly advantageous in this context is reliable filming at temperatures below 10° C., thereby enabling processing without the addition of plasticizer. The reproducible coalescence of the latex particles permits the formulation of delayed-release pharmaceutical forms.

If the above-described crystallization of emulsifiers occurs, it constitutes a considerable reduction in the quality of medicaments. For the purposes of medicament safety, therefore, the crystallization of the emulsifiers after drying should be prevented. This effect is obviously achieved by structural interaction of the emulsifier with the polymer. The dispersions of the invention therefore permit the development of more reliable delayed-release pharmaceutical forms.

The invention is suitable in particular for the provision of pharmaceutical forms comprising the active substances given below.

Therapeutic Categories:

Analgesics, antirheumatics, antiallergics, anti-arrhythmics, beta receptor blockers, calcium channel blockers, inhibitors of the renin-angiotensin system, broncholytics/antasthmatics, cholinergics, diuretics, circulation promoters, gout agents, influenza agents, coronary agents, lipid reducers, gastrointestinal agents, psychopharmaceuticals, platelet aggregation inhibitors, urological agents, venous therapeutic agents, vitamins and minerals.

Active substances

Morphine and its derivatives, tramadol, acetylsalicylic acid, diclofenac, indomethacin, lonazolac, ibuprofen, ketoprofen, propyphenazone, naproxen, paracetamol, flurbiprofen, dimetindene, quinidine, metoprolol, propanolol, oxprenolol, pindolol, atenolol, metoprolol, disopyramide, verapamil, diltiazem, gallopamil, nifedipine, nicardipine, nisoldipine, nimodipine, amlodipine, theophylline, salbutamol, terbutaline, ambroxol, aminophylline, choline theophyllinate, pyridostigmine, piretanide, furosemide, pentoxifylline, naftidrofuryl, buflomedil, xanthinol nicotinate, bencyclane, allopurinol, norephedrine, chlorphenamine, isosorbide mononitrate, isosorbide dinitrate, glycerol trinitrate, molsidomine, bezafibrate, fenofibrate, gemfibrozil, cerivastatin, pravastatin, fluvastatin, lovastatin, atorvastatin, simvastatin, xanthinol, methoclopramide, amitriptyline, dibenzepine, venla-faxine, thioridazine, oxazepam, lithium, nitro-furantoin, dry plant extract, ascorbic acid and potassium and the salts thereof used pharmaceutically.

EXAMPLES

Investigation Methods:

Solids content: 1 g of dispersion is dried in an oven at 110° C. for 3 hours in accordance with Pharm. Eur. 2.2.32 method d.

pH: Determined in accordance with Pharm. Eur. Method 2.2.3.

Dynamic viscosity: determined using a Brookfield viscometer (UL adapter/30 min$^{-1}$/20° C.)

Particle size: determined from dilute dispersion using a Nanosizer (Coulter).

Coagulum fraction: 100 g of dispersion are passed through a precision-weighed sieve with a mesh size of 0.09 mm (mesh number 90, ISO) and washed through with purified water until the runnings are clear. Sieve and residue are dried to constant weight at 105° C. and weighed precisely. The weight difference is calculated as a % of the amount of dispersion investigated.

Crystallization of the Emulsifier:

About 0.3 g of dispersion is placed on a slide and dried at <10° C. for at least 12 h. The crystallization of the emulsifier in the dried film is subsequently examined under a polymerization microscope at 400-fold magnification. Crystallization is evident from the coloured birefringences; amorphous regions appear dark.

1–5. Variation of the Polymer Composition

To prepare the dispersion, a reaction vessel is charged with 55.0 kg of water and 328 g of polyoxyethylene-20-cetyl ether are dissolved therein. Following dissolution, the monomers as per table 1, 6.6 kg of ethyl acrylate, 7.1 kg of methyl methacrylate and 0.3 kg of methacrylic acid are added and the mixture is emulsified at 30° C.

To start the reaction, the water-soluble initiators are added (0.22 g of iron(II) sulphate in solution in 160 g of water, 22.0 g of ammonium peroxodisulphate and 30.8 g of sodium disulphate, each in solution in 320 g of water). After the temperature peak has been reached, the batch is cooled. At about 50° C., 754 g of emulsifier as in the table are added for subsequent stabilization. After 40° C. has been reached, 6.7 g of ammonium peroxodisulphate in solution in 160 g of water are added for the after-reaction and the dispersion is filtered and then deodorized.

| Ex. | Ethyl acrylate [part] | Methyl meth-acrylate [part] | Meth-acrylic acid [part] | Solids content [%] | pH | Dynamic viscosity [mPa*s] | Particle size $r_{NS}$ [nm] | Crystallization of the emulsifier |
|---|---|---|---|---|---|---|---|---|
| 1 | 70 | 30 | 0 | 30.6 | 2.7 | <50 | 60.3 | no |
| 2 | 69 | 30 | 1 | 30.9 | 8.3 | <50 | 76.0 | no |
| 3 | 68 | 29 | 3 | 30.6 | 2.8 | <50 | 57.5 | no |
| 4 | 66 | 29 | 5 | 30.7 | 2.7 | <50 | 61.8 | no |
| 5 | 63 | 27 | 10 | 30.3 | 2.6 | <50 | 89.0 | no |

6–15. Variation of the Emulsifier

To prepare the dispersion, a reaction vessel is charged with 55.0 kg of water and 328 g of emulsifier in accordance with the table are dissolved therein. Following dissolution, 16.6 kg of ethyl acrylate, 7.1 kg of methyl methacrylate and 0.3 kg of methacrylic acid are added and the mixture is emulsified at 30° C. To start the reaction, the water-soluble initiators are added (0.22 g of iron(II) sulphate in solution in 160 g of water, 22.0 g of ammonium peroxodisulphate and 30.8 g of sodium disulphate, each in solution in 320 g of water). After the temperature peak has been reached, the batch is cooled. At about 50° C., 754 g of emulsifier as in the table are added for subsequent stabilization. After 40° C. has been reached, 6.7 g of ammonium peroxodisulphate in solution in 160 g of water are added for the after-reaction and the dispersion is filtered and then deodorized.

subsequent stabilization. After 40° C. has been reached, 6.7 g of ammonium peroxodisulphate in solution in 160 g of water are added for the after-reaction and the dispersion is filtered and then deodorized.

17. Dispersion Preparation by Emulsion Polymerization in a Dual Batch Process

For the 1st batch of the dispersion, a reaction vessel is charged with 23.0 kg of water and 512 g of emulsifier in accordance with the table are dissolved therein. Following dissolution, 8.30 kg of ethyl acrylate, 3.55 kg of methyl methacrylate and 0.14 kg of methacrylic acid are added and the mixture is emulsified at 30° C.

To start the reaction, the water-soluble initiators are added (0.22 g of iron(II) sulphate, 11.0 g of ammonium peroxodisulphate and 15.4 g of sodium disulphate, each in solution

| Ex. | Emulsifiers | HLB | Solids content [%] | PH | Dynamic viscosity [mPa*s] | Particle size $r_{NS}$ [nm] | Coagulum content [%] | Crystallization of the emulsifier |
|---|---|---|---|---|---|---|---|---|
| 6 | Polyoxyethylene-100-isononylphenol | 19.1 | 50.4 | 2.5 | 6800 | 81 | <0.5 | yes |
| 7 | polyoxyethylene-100-stearyl ether | 18.8 | 50.6 | 2.4 | 760 | 88 | n.d. | yes |
| 8 | Polyoxyethylene-50-nonylphenol | 18.3 | 50.2 | 2.7 | 1225 | 76 | 0.04 | yes |
| 9 | Polyoxyethylene-35-nonylphenol | 17.5 | 51.7 | n.d. | n.d. | 72 | 0.1 | yes |
| 10 | Polyoxyethylene-25-cetyl stearate | 16.2 | 48.7 | 2.6 | 200 | 77 | 0.2 | no |
| 11 | Polyoxyethylene-20-sorbitan monopalmitate | 16.0 | 45.5 | 2.7 | n.d. | 112 | n.d. | no |
| 12 | Polyoxyethylene-16-tert-octylphenol | 15.8 | 50.6 | 2.5 | 2800 | 90 | 0.06 | no |
| 13 | Polyoxyethylene-20-cetyl ether | 15.7 | 50.5 | 2.5 | 350 | 82 | 0.06 | no |
| 14 | Polyoxyethylene-20-sorbitan monostearate | 14.9 | n.d. | n.d. | n.d. | n.b. | >10 | n.d.* |
| 15 | Polyoxyethylene-20-sorbitan monooleate | 15.0 | 47.7 | 2.6 | 480 | 91 | 8.21 | n.d.* | n.d. *) not determinable, owing to coagulation

16–18. Variation of the Preparation Process

16. Dispersion Preparation by Emulsion Polymerization by the Single-Stage Batch Process To prepare the dispersion, a reaction vessel is charged with 55.0 kg of water and 328 g of polyoxyethylene-20-cetyl ether in accordance with the table are dissolved therein. Following dissolution, 16.6 kg of ethyl acrylate, 7.1 kg of methyl methacrylate and 0.3 kg of methacrylic acid are added and the mixture is emulsified at 30° C.

To start the reaction, the water-soluble initiators are added (0.22 g of iron(II) sulphate in solution in 160 g of water, 22.0 g of ammonium peroxodisulphate and 30.8 g of sodium disulphate, each in solution in 320 g of water). After the temperature peak has been reached, the batch is cooled. At about 50° C., 754 g of emulsifier as in the table are added for in 160 g of water). After the temperature peak has been reached, the batch is cooled to 50° C.

For the 2nd batch, 570 g of emulsifier are added to the 1st batch and the mixture is stirred for 30 minutes. Subsequently, in analogy to the 1st batch, the same amount of monomers is added, the batch is stirred for 10 minutes and the initiators are added (11.0 g of ammonium peroxodisulphate and 15.4 g of sodium disulphite, each in solution in 160 g of water). After the end of the reaction, the batch is cooled to 40° C. and initiator (6.7 g of ammonium peroxodisulphate in solution in 160 g of water) is added for the after-reaction. For deodorization, the dispersion is adjusted to a pH of about 8 using dilute sodium hydroxide solution in a reaction vessel, and 10–15% of the dispersion water are distilled off. Thereafter the dispersion is diluted to a solids content of approximately 30%. The dispersion thereafter is filtered.

18. Dispersion Preparation by Emulsion Polymerization by the Feed Process

In a glass reactor, 2370 g of water and 5.0 g of emulsifier as per the table are heated to 80° C. with stirring. During this time, a preemulsion consisting of 1800 g of water, 64.9 g of emulsifier, 3.0 g of ammonium peroxodisulphate, 1245.6 g of ethyl acrylate, 532.8 g of methyl methacrylate and 21.6 g of methacrylic acid is prepared using a high-shear stirrer. The amount of initiator (1.2 g of ammonium peroxodisulphate in solution in 30 g of water) provided for the initiation of the reaction is added to the initial charge and the preemulsion is metered into the initial charge over the course of four hours at 80° C. After the end of the feed, the resulting dispersion is stirred at 80° C. for two hours more, then cooled to room temperature and adjusted to a pH of approximately 8 using dilute sodium hydroxide solution, and 10–15% of the dispersion water are distilled off. The dispersion is subsequently diluted to a solids content of about 30%. Thereafter, the dispersion is filtered.

The dispersions obtained were tested for the properties stated in the table. The table lists the analytical values of the dispersions in accordance with the abovementioned preparation conditions.

| Dispersion | Solids content [%] | pH | Dynamic viscosity [mPa*s] | Particle size $r_{NS}$ [nm] | Crystallization of the emulsifier |
|---|---|---|---|---|---|
| 16 | 30.9 | 8.3 | <10 | 76 | no |
| 17 | 29.6 | 8.3 | <10 | 78 | no |
| 18 | 30.2 | 8.3 | <10 | 90 | no |

19. Use of the Dispersion as Coating Agent:

a) Coatings on Potassium Chloride Crystals.

In a fluid-bed coating unit (GPCG 1, GLATT) 800 g of KCl crystals (0.3–0.8 mm) are coated with a spray suspension of 373.3 g of inventive dispersion from example 12, 112 g of talc, 0.95 g of antifoam emulsion and 412 g of purified water. The air entry temperature is 30° C. and the spray pressure at the nozzle (diameter 1.2 mm) is 2.0 bar. The spraying time is about 90 minutes. After drying at room temperature for 16 hours, uniform coated crystals are obtained.

The release of the potassium chloride crystals was measured over 6 hours in a paddle device at 100 rpm in 900 ml of water. The potassium chloride content was determined by potentiometry.

The release profile of the potassium chloride crystals coated with the inventive dispersion indicates uniform delayed release over 6 h (see FIG. 1/2).

20. Use of the Dispersion as Binder:

Matrix tablets are produced with a total mass of 600 mg and a diprophylline content of 150 mg. For 1.2 kg of matrix tablets, 300 g of diprophylline are mixed with 400 g of calcium hydrogenphosphate dihydrate (0.1–0.2 mm) in the STEPHAN UM 12 and the mixture is subsequently wetted with the inventive dispersion from example 12. After drying at 40° C. for 6 h, the tablet composition is passed through a 1 mm sieve, mixed with 12 g of magnesium stearate and compressed on a KORSCH eccentric tabletting press at 10 kN. The resulting tablets have a slight gloss, possess good mechanical strength, and exhibit a uniform release rate over 6–7 hours.

The release profile of the matrix tablets containing diprophylline likewise shows uniform delayed release (FIG. 2/2). The release of active substance was determined over 6 hours in a paddle device at 50 rpm in 900 ml of water using a Perkin-Elmer Lambda 20 UV-VIS spectrometer at 274 nm.

The invention claimed is:

1. A dispersion, comprising:
   a solids content of 10–70% by weight comprising
   a) from 90 to 99% by weight of a methacrylate copolymer comprising at least 90% by weight of a (meth) acrylate monomer containing at least one neutral radical and having a glass transition temperature Tg of from −20° C. to +20 C. as determined by the DSC method, and
   b) 1–10% by weight of a nonionic emulsifier having an HLB of from 15.2 to 17.3.

2. The dispersion according to claim 1, wherein the methacrylate copolymer comprises from 20 to 50% by weight of methyl methacrylate, and from 80 to 50% by weight of ethyl acrylate.

3. The dispersion according to claim 1, wherein the nonionic emulsifier is selected from the group consisting of ethoxylated fatty acid ester, ethoxylated fatty acid ethers, ethoxylated sorbitan ethers, ethoxylated alkyl-phenols, glycerol esters, glycerol sugar esters, wax derivatives and mixtures thereof.

4. The dispersion according to claim 1, wherein the nonionic emulsifier is selected from the group consisting of polyoxyethyleneglycerol monolaurate, polyoxyethyleneglycerol monostearate, polyoxyethylene-20-cetyl stearate, polyoxyethylene-25-cetyl stearate, polyoxyethylene (25)-oxypropylene monostearate, polyoxyethylene-20-sorbitan monopalmitate, poly-oxyethylene-16-tert-octylphenol, polyoxyethylene-20-cetyl ether, polyethylene glycol(1000) monocetyl ether, ethoxylated castor oil, polyoxyethylene sorbitol-lanolin derivatives, polyoxyethylene(25)propylene glycol stearate, polyoxyethylenesorbitol esters, polyoxyethylene-20-sorbitan monopalmitate, polyoxyethylene-16-tert-octylphenol, polyoxyethylene-20-cetyl ether and mixtures thereof.

5. A process for preparing the dispersion claimed in claim 1, comprising: emulsion polymerizing said (meth)acrylate monomer.

6. A pharmaceutical composition, comprising:
   the dispersion as claimed in claim 1, and a pharmaceutically active substance.

7. The pharmaceutical composition as claimed in claim 6, wherein said pharmaceutically active substance comprises an active substance selected from the group consisting of morphine, morphine derivatives, tramadol, acetylsalicylic acid, diclofenac, indomethacin, lonazolac, ibuprofen, ketoprofen, propyphenazone, naproxen, paracetamol, flurbiprofen, dimetindene, quinidine, metoprolol, propanolol, oxprenolol, pindolol, atenolol, metoprolol, disopyramide, verapamil, diltiazem, gallopamil, nifedipine, nicardipine, nisoldipine, nimodipine, amlodipine, theophylline, salbutamol, terbutaline, ambroxol, aminophylline, choline theophyllinate, pyridostigmine, piretanide, furosemide, pentoxifylline, naftidrofuryl, buflomedil, xanthinol nicotinate, bencyclane, allopurinol, norephedrine, chlorphenamine, isosorbide mononitrate, isosorbide dinitrate, glycerol trinitrate, molsidomine, bezafibrate, fenofibrate, gemfibrozil, cerivastatin, prava-statin, fluvastatin, lovastatin, atorvastatin, simvastatin, xanthinol, methoclopramide, amitriptyline, dibenzepine, venlafaxine, thioridazine, oxazepam, lithium, nitrofurantoin, dry plant extract, diprophylline, ascorbic acid, potassium, pharmaceutical salts thereof and mixtures thereof.

8. A pharmaceutical composition, comprising:
an active pharmaceutical substance and the dispersion as claimed in claim 1, wherein said active pharmaceutical substance is bound or coated with said dispersion.

9. A method for coating a pharmaceutical composition, comprising:
encapsulating the pharmaceutical composition with the dispersion claimed in claim 1.

10. The dispersion according to claim 1, wherein the methacrylate copolymer comprises from 20 to 50% by weight of methyl methacrylate and from 80 to 50% by weight of ethyl acrylate and from 0 to 10% by weight of methacrylic acid.

11. The dispersion according to claim 1, wherein the nonionic emulsifier is polyoxyethylene-25-cetyl stearate.

12. The pharmaceutical composition claimed in claim 7, wherein said pharmaceutical salts are potassium salts.

13. The dispersion as claimed in claim 1, wherein said (meth)acrylate monomer contains $C_1$ to $C_4$ alkyl radicals.

14. The dispersion as claimed in claim 1, wherein said (meth)acrylate monomer is methyl methacrylate, ethyl acrylate, methyl acrylate or mixtures thereof.

15. The dispersion as claimed in claim 1, wherein not more than 10% by weight of said (meth)acrylate monomers contains an anionic radical.

16. The dispersion as claimed in claim 1, wherein said copolymer comprises methacrylic acid.

17. The dispersion as claimed in claim 1, wherein said emulsifier is polyoxyethylene-25-cetyl stearate, polyoxyethylene-20-sorbitan monopalmitate, polyoxyethylene-16-tert-octylphenol, polyoxyethylene-20-cetyl ether or mixtures thereof.

18. A coating agent, comprising:
the dispersion as claimed in claim 1.

19. The dispersion according to claim 1, wherein said emulsifier does not crystallize after drying said dispersion.

* * * * *